United States Patent
Schaefer et al.

(10) Patent No.: US 11,407,967 B2
(45) Date of Patent: Aug. 9, 2022

(54) DEVICE AND METHOD FOR ACCOMMODATING A DISPOSABLE CONTAINER

(71) Applicant: Sartorius Stedim Biotech GmbH, Goettingen (DE)

(72) Inventors: Jan Schaefer, Edermuende (DE); Hannes Schmid, Felsberg (DE)

(73) Assignee: Sartorius Stedim Biotech GmbH, Goettingen (DE)

(*) Notice: Subject to any disclaimer, the term of this patent is extended or adjusted under 35 U.S.C. 154(b) by 558 days.

(21) Appl. No.: 15/777,685

(22) PCT Filed: Oct. 21, 2016

(86) PCT No.: PCT/EP2016/001748
§ 371 (c)(1),
(2) Date: May 21, 2018

(87) PCT Pub. No.: WO2017/157404
PCT Pub. Date: Sep. 21, 2017

(65) Prior Publication Data
US 2018/0334645 A1    Nov. 22, 2018

(30) Foreign Application Priority Data
Mar. 15, 2016    (DE) .................... 10 2016 003 136.0

(51) Int. Cl.
C12M 1/00    (2006.01)
C12M 3/00    (2006.01)
C12M 1/34    (2006.01)

(52) U.S. Cl.
CPC ............ *C12M 21/02* (2013.01); *C12M 23/26* (2013.01); *C12M 23/28* (2013.01); *C12M 23/48* (2013.01);

(Continued)

(58) Field of Classification Search
None
See application file for complete search history.

(56) References Cited

U.S. PATENT DOCUMENTS

| | | | |
|---|---|---|---|
| 2011/0310696 A1 | 12/2011 | Goodwin et al. | |
| 2015/0210970 A1* | 7/2015 | Hellingwerf | C12M 41/06 435/257.1 |
| 2018/0119084 A1* | 5/2018 | Tuohey | C12N 7/00 |

FOREIGN PATENT DOCUMENTS

| | | |
|---|---|---|
| DE | 40 28 871 | 3/1992 |
| DE | 697 18 178 | 10/2003 |

(Continued)

OTHER PUBLICATIONS

International Search Report and Written Opinion dated Jan. 5, 2017.
(Continued)

*Primary Examiner* — William H. Beisner
(74) *Attorney, Agent, or Firm* — Gerald E. Hespos; Michael J. Porco (57) ABSTRACT

A device (1) for accommodating a disposable container (44) has a receptacle (10) with at least one receptacle wall (16) that defines an interior of the receptacle (10) for accommodating the disposable container (44). The device includes a temperature control unit for controlling the temperature of the receptacle wall (16). A lighting device (50) is located on an inner face of the receptacle wall (16) that faces the interior of the receptacle (10) and that has the temperature controlled by the temperature control unit. The lighting device (50) is designed to emit light into the interior of the receptacle (10).

15 Claims, 5 Drawing Sheets (52) U.S. Cl.
CPC ............ *C12M 31/02* (2013.01); *C12M 31/10* (2013.01); *C12M 41/12* (2013.01)

(56) References Cited

FOREIGN PATENT DOCUMENTS

| DE | 10 2005 006 055 | 8/2006 | | |
|---|---|---|---|---|
| DE | 20 2007 013 406 | 12/2007 | | |
| DE | 202007013406 U1 | * 12/2007 | ............ | C12M 31/10 |
| DE | 10 2010 007 559 | 8/2011 | | |
| DE | 10 2010 018 678 | 11/2011 | | |
| DE | 102012013587 A1 | * 1/2014 | ............ | C12M 21/02 |
| EP | 2 725 092 | 4/2014 | | |
| WO | 2006/032084 | 3/2006 | | |
| WO | 2015/039034 | 3/2015 | | |

OTHER PUBLICATIONS

English Translation of International Preliminary Report on Patentability for Application No. PCT/EP2016/001748 dated Sep. 18, 2018.
European Examination Report dated Aug. 9, 2019.

\* cited by examiner

DEVICE AND METHOD FOR ACCOMMODATING A DISPOSABLE CONTAINER

BACKGROUND

Field of the Invention

The invention relates to a device and a method for receiving a disposable vessel.

Description of the Related Art

Bioreactors and pallet tanks serve as devices for receiving, storing and/or cultivating biological media such as for example fluids and/or cell cultures. Biological media may be provided in disposable vessels which may enclose a volume from a few liters up to several hundred liters. The biological media are inserted, within a disposable vessel, into the bioreactor, in which they are temperature-controlled to a predeterminable temperature over a predetermined time period, normally several hours in duration. Various tests on the biological medium may also be performed in a bioreactor of said type.

The handling of a bioreactor may be performed under clean room conditions, such that particularly high demands are placed on the quality control for the bioreactor.

In so-called single-use processes, it is possible in particular for disposable pouches to be used as disposable vessels. Both upstream and downstream, the use of disposable vessels has proven to save time and costs and to be reliable in terms of process technology. Whereas experience with cell culture processes and some microbial cultures has already been gained, it has hitherto scarcely been possible to realize processes with phototrophic organisms such as algae and/or plant cell cultures, in particular for a production scale of over 50 liters.

The invention is based on the object of realizing a facility of the type mentioned in the introduction for receiving a disposable vessel with phototrophic organisms, which is suitable in particular for a production scale of over 50 liters.

SUMMARY

A first aspect relates to a device for receiving a disposable vessel, having a receiving vessel with at least one receiving vessel wall which delimits a vessel interior space of the receiving vessel for receiving the disposable vessel. The device furthermore has a temperature-control unit for controlling the temperature of the receiving vessel wall. On an inner side, facing toward the vessel interior space, of the receiving vessel wall which is temperature-controlled by the temperature-control unit, there is arranged an illumination device which is designed to radiate light into the vessel interior space of the receiving vessel.

The device may be formed as a bioreactor and/or pallet tank, which may be designed for receiving disposable vessels with a volume from approximately 1 liter to approximately 2000 liters, preferably with a volume from approximately 200 liters to approximately 1000 liters. The device may be formed as a system with multiple components, in particular with or without a disposable vessel as an associated component. The device may be designed in particular for receiving disposable vessels containing a biological medium such as a fluid which is to be stored, temperature-controlled, cultivated and/or tested in some other way in the system over a predetermined time period. The biological medium may be in the form of a cell culture, and/or may have phototrophic organisms.

The disposable vessel may be in the form of a disposable pouch with flexible pouch walls, in particular with transparent plastics walls. The disposable vessel may, in its interior, have agitation components which can be coupled to an agitation device of the device in order to thereby permit mixing of the content of the disposable vessel.

The receiving vessel of the device provides the vessel interior space that is designed for receiving the disposable vessel. Here, the vessel interior space may be designed for receiving a predeterminable type of disposable vessel, that is to say for example a disposable vessel from a predeterminable manufacturer and/or with a predeterminable fill volume. Here, the receiving vessel wall or walls define the vessel interior space. Here, the receiving vessel walls need not fully surround and/or border the vessel interior space. Accordingly, the receiving vessel may for example have an agitation opening through which an agitation device can be connected to the disposable vessel arranged in the vessel interior space. An agitation device of said type is preferably formed on the upper end of the receiving vessel. The receiving vessel may thus be formed in particular without a cover, and/or so as to be open at the top.

In the context of this invention, the expressions "top", "bottom", "laterally", "vertically", "horizontally", "height", "lateral" etc. relate to the reference system of the earth, in which the system or the device is arranged in an operational position.

The disposable vessel is preferably inserted into the receiving vessel so as to lie on a base of the receiving vessel and so as to be in direct physical contact with the receiving vessel walls of the receiving vessel, in particular in contact with the base of the receiving vessel and/or with the receiving vessel walls that adjoin the base.

The at least one receiving vessel wall can be temperature-controlled by means of the temperature-control unit. The temperature-control unit can control the temperature of the receiving vessel wall to a predeterminable, in particular settable temperature. The temperature-control unit may be designed in particular for cooling the receiving vessel wall. Here, the temperature-control unit may either be arranged directly on an outer side, averted from the vessel interior space, of the receiving vessel wall or so as to be at least in direct heat-exchanging contact with the receiving vessel wall. Here, the receiving vessel wall may exhibit high thermal conductance, that is to say may for example be metallic.

The receiving vessel may have at least one openable and closable door through which the disposable vessel can be inserted into the vessel interior space.

The illumination device is arranged in the vessel interior space, which illumination device is, in an operational position of the device, arranged between the receiving vessel wall and the disposable vessel. In the operational position of the device, a disposable vessel is inserted into the device. The disposable vessel need not be a constituent part of the device. The disposable vessel may however be formed as a constituent part of the device.

The illumination device may be arranged in the vessel interior space so as to be in heat-exchanging contact with the temperature-controlled receiving vessel wall. Here, it is the case in particular that the illumination device is temperature-controlled, for example cooled, by means of the temperature-control unit. This permits a removal of the illumination-induced heat that can be generated during operation of the illumination device. Here, the illumination device requires no dedicated cooling arrangement, but can be temperature-controlled or cooled by means of the temperature-control unit of the device.

The device is suitable in particular for receiving disposable vessels with phototrophic organisms or cell cultures. The medium situated in the disposable vessel can be irradiated by means of the light radiated by the illumination device. Here, the walls of the disposable vessel are preferably transparent for at least the light wavelength(s) at which the illumination device radiates light into the vessel interior space.

In the context of this invention, the expression "light" does not necessarily mean visible light, but may rather relate to electromagnetic radiation with a wavelength from approximately 50 nm to approximately 50 μm. The expression thus also encompasses in particular ultraviolet and infrared light. The wavelength or the wavelength range of the light radiated by the illumination device may be adapted to particular requirements of the medium in the disposable vessel. The illumination device may have one or more light sources which are oriented such that they radiate light in the direction away from the receiving vessel wall toward the vessel interior space, in particular in a direction away from the receiving vessel wall toward the spatial region in which the disposable pouch is arranged in the operational position, for example toward a central point and/or a central axis of the vessel interior space.

The illumination device may, in the operational position, both directly adjoin the receiving vessel wall and directly adjoin the disposable vessel. Owing to this proximity between disposable vessel and illumination source, particularly efficient radiation of light into the interior of the disposable vessel with greatly reduced losses is made possible. At the same time, by means of the temperature control using the temperature-control unit, an adverse, overly intense generation of heat by the illumination device can be avoided, such as could otherwise lead both to damage of the cell cultures and to damage of a wall, formed from plastic, of the disposable vessel.

The device is thus particularly suitable for receiving disposable vessels which have a culture volume for a microbial culture, a cell culture, a culture of cell and/or tissue conglomerates of plant and/or animal cells and/or hybrid forms.

The device may furthermore have a controller which serves for controlling the light output by the illumination device. The illumination device may for example radiate modulated and/or non-modulated electromagnetic radiation, or else coherent electromagnetic radiation, such as for example laser light. The illumination device may be actuated so as to radiate a controllable quantity of light during controllable time periods. Here, the illumination device can in particular also be deactivated.

In one embodiment, the illumination device has at least one light source which is arranged at a position of the inner side of the receiving vessel wall which is temperature-controlled by the temperature-control unit directly at an outer side, averted from the vessel interior space, of the receiving vessel wall. Here, it is possible in particular for all light sources of the illumination device to be arranged at positions of the inner side of the receiving vessel wall which are temperature-controlled at the outer side. Since, in this embodiment, heat generated at the one or more light sources can be removed in a very efficient manner, this embodiment is particularly efficient. Thus, in this embodiment, the light source of the illumination device is arranged on one side of the receiving vessel wall, whereas the temperature-control unit is arranged at the opposite side of the receiving vessel wall. Here, the temperature control through the receiving vessel wall may act on the light source, which is arranged either so as to be in direct physical contact with the receiving vessel wall or so as to be spaced apart from the receiving vessel wall only by a carrier. As a carrier, use may be made of a substrate, in particular a substrate which is thermally conductive at least at certain points. The temperature control on the outer side of the receiving vessel wall may be performed for example by means of a temperature-control medium, which controls the temperature of the receiving vessel wall at the outer side.

In one embodiment, the illumination device has a multiplicity of light sources which are arranged so as to be distributed over at least 50% of the area of the inner side of all lateral receiving vessel walls. Through the use of a multiplicity of light sources, the luminous power and/or the number of photons that can be radiated into the vessel interior space is increased. The light sources may be arranged such that light sources are arranged on as many receiving vessel walls as possible. One aim here may be to achieve substantially uniform illumination over the outer surfaces of the vessel. In this embodiment, light sources are arranged at least on 50% of the lateral receiving vessel walls. The lateral receiving vessel walls are in this case those walls of the receiving vessel which delimit the vessel interior space in a lateral direction. These are, for example in the case of a substantially cylindrical, upright receiving vessel, all of the walls of the cylinder casing without the cylinder base and without the cylinder cover. It is preferably possible here for the light sources to be arranged on substantially all lateral receiving vessel walls. Here, "substantially" means that those surfaces of the lateral receiving vessel walls on which a door and/or a viewing window is arranged may remain omitted. Here, the light sources may be arranged on the receiving vessel walls substantially from the bottom to the top, in particular from a foot of the receiving vessel up to an intended fill height.

In one embodiment, the illumination device has a multiplicity of actuatable LEDs as light sources. In this way, it is possible for both modulated and non-modulated radiation to be output. LEDs are suitable as particularly efficient light sources, because LEDs generate relatively little heat in relation to the quantity of light output, whereby the heat generation can be reduced and, at the same time, the radiated luminous power can be increased. Furthermore, LEDs can be formed with a small structural height, such that these light sources can be arranged substantially areally on the inner side of the receiving vessel wall, without overly reducing the volume of the vessel interior space and without forming significant projections in the interior of the receiving vessel, which would impede an insertion of the disposable vessel.

In one embodiment, the illumination device radiates at least 90% of the radiated luminous power with a predetermined wavelength or with a predetermined wavelength spectrum of between 50 nm and 50 μm. The illumination device may thus be designed to radiate electromagnetic radiation with the predetermined wavelength or a predetermined wavelength spectrum. This may in particular involve laser light and/or light from LEDs. The predetermined wavelength or the predetermined wavelength spectrum may be adapted to the content of the disposable vessel, in particular to wavelengths that influence the metabolism of the cells situated therein. Here, the illumination device may for example be designed to radiate at least 90% of the radiated luminous power at the predetermined wavelength or in the predetermined wavelength spectrum.

In one embodiment, the illumination device is designed to radiate light by means of exchangeable light sources which have different radiation spectra. Accordingly, the device can be used firstly for a culture medium which requires electromagnetic radiation of a first wavelength and/or of a first wavelength spectrum, which is radiated by a first set of light sources of the illumination device. The light sources can subsequently be exchanged for light sources that radiate predominantly light of a second wavelength and/or of a second wavelength spectrum, which may be suitable for a different type of cells or metabolism influencing. The exchangeable form of the light sources serves firstly for enabling damaged individual light sources to be exchanged if required and for the variation of the radiation spectrum of the illumination device, for example by exchange of all light sources for light sources with different radiation characteristics. In this embodiment, the illumination device may in particular have a holder which is arranged and/or fastened in the interior of the receiving vessel, and may furthermore have at least one exchangeable carrier on which the light sources are arranged. Said carrier may for example be of strip-shaped form, wherein multiple light sources may be arranged on each strip. The carriers, together with the light sources arranged thereon for example as a subassembly, can be dismounted from the holder of the illumination device and exchanged. The carriers of the light sources can in particular be individually exchanged and/or individually fastened to the holder.

In one embodiment, an external shape of an outer side, averted from the vessel interior space, of the illumination device is adapted to an internal shape of the inner side of the receiving vessel wall. Here, the external shape of the illumination device is thus formed as a complementary counterpart to the internal shape of the receiving vessel wall. As a counterpart of said type, the outer wall of the illumination device bears closely against the inner wall of the receiving vessel wall. In this way, the heat conduction between the illumination device and the receiving vessel wall is improved. Here, a further layer, for example a thermally conductive foil and/or an adhesive, may be arranged between the receiving vessel wall and the illumination device.

In a refinement of this embodiment, the external shape of the illumination device is of convex form, whereas the internal shape of the receiving vessel wall is of concave form. For example, the receiving vessel may be substantially in the form of an upright cylinder which has a substantially circular or oval cross section. The inner side of the receiving vessel is thus concave. Here, the outer side of the illumination device is adapted to said concave shape by virtue of said outer side itself being of convex form in the direction toward the inner side of the outer vessel wall. Here, too, the heat conduction between the illumination device and the receiving vessel wall is increased.

In one embodiment, the illumination device is designed to emit light with a luminous power of up to approximately 3000 µmol/m2s into the vessel interior space. With such high radiation power, intense generation of heat can occur. This heat generation is compensated by means of the temperature-control unit. Particularly efficient cultivation of biological media is possible by means of the high luminous power.

In one embodiment, the illumination device has a multiplicity of light sources arranged on a strip, wherein the strip is arranged substantially vertically along the receiving vessel wall. It is thereby made possible for a multiplicity of light sources to be arranged on the receiving vessel wall simultaneously. This is advantageous in particular in the case of rounded and/or curved receiving vessel walls, on which vertical strips as carriers of the light sources are arranged. The strips may be formed either as carriers of multiple light sources spaced apart vertically from one another, or so as to support in each case one elongate light source, for example one elongate and/or rod-shaped light source. A multiplicity of such strips may be arranged in the receiving vessel along the curvature of the receiving vessel wall. The strips may be arranged at a position in the receiving vessel at which the receiving vessel wall is formed with an only one-dimensional curvature, that is to say has a curvature only in one direction of extent. The receiving vessel wall may be of non-curved form in a direction perpendicular to the direction of curvature. The strips may be arranged in the receiving vessel so as to extend along the receiving vessel wall said non-curved direction of extent, in which the receiving vessel wall is of substantially straight form. The strips may be formed as a carrier and/or substrate for the light sources. Furthermore, the strips may be formed as thermal bridges between the light sources and the receiving vessel wall, and/or may have such thermal bridges. Furthermore, a thermally conductive foil and/or an adhesive layer may be arranged between the receiving vessel wall and the strip.

In one embodiment, in an operational position of the device, the disposable vessel is in physical contact with the illumination device. This means that the illumination device is arranged such that, in the operational position of the device, in which the disposable vessel has been inserted into the receiving vessel, the disposable vessel lies directly against the illumination device. This enables the content of the disposable vessel to be illuminated in a particularly efficient manner or with low losses.

In one embodiment, an in particular transparent resin layer and/or lacquer layer with a thickness of up to approximately 1 mm is arranged over light sources of the illumination device. Sharp edges, which could damage the disposable vessel, of the illumination sources can be smoothed by means of the resin layer and/or lacquer layer. Furthermore, by means of the resin layer and/or lacquer layer, projections can be reduced in order to smooth the receiving vessel walls that are narrowed by the illumination device. An epoxy resin may be used as resin. The resin layer and/or lacquer layer is in particular of transparent form for the one or more wavelengths radiated by the illumination device. The resin layer and/or lacquer layer on the light sources preferably has a maximum thickness of approximately half of one millimeter.

In one embodiment, the illumination device has at least one thermal bridge between light sources of the illumination device and the temperature-controlled receiving vessel wall. Such thermal bridges improve the removal of heat from the light sources via the receiving vessel wall.

In one embodiment, the temperature-control unit is designed to impart a heat removal power of up to at least 8 kW, preferably at least 10 kW, particularly preferably up to at least 20 kW. Such intense heat removal power of the temperature-control unit may permit an approximately equally great generation of heat during the illumination of the content of the disposable vessel. Thus, this embodiment permits particularly bright, intense and highly powerful illumination of a biological medium.

In one embodiment, the receiving vessel wall is formed at least partially as a temperature-control cavity wall. Here, the temperature-control unit is designed to control the temperature of the vessel interior space by means of a temperature-control medium arranged in the temperature-control cavity wall.

The temperature-control cavity wall is formed in the receiving vessel walls of the receiving vessel can be formed as part of a closed temperature-control circuit. The temperature-control cavity wall may be formed as part of the receiving vessel walls. The temperature-control cavity wall may be formed as a double wall with a temperature-control inner wall and a temperature-control outer wall. Here, the temperature-control inner wall may face toward the vessel interior space of the receiving vessel, and the temperature-control outer wall may be averted from the vessel interior space.

The temperature-control medium is formed and arranged in a cavity between the temperature-control inner wall and the temperature-control outer wall. The temperature-control unit controls the temperature of the vessel interior space, in particular the content of the disposable vessel and/or the illumination device, by means of the temperature-control medium. For this purpose, a controller may be provided, by means of which the temperature and/or the pressure of the temperature-control medium in the temperature-control cavity wall can be controlled and/or set. The controller may be formed as part of the temperature-control unit. The temperature-control unit may thus comprise the controller and/or the temperature-control medium arranged in the temperature-control cavity wall.

The interior of the temperature-control cavity wall may be formed as a free cavity or with at least one flow-guiding element for guiding the flow of the temperature-control medium through the temperature-control cavity wall.

The two walls of the temperature-control cavity wall, that is to say a temperature-control inner wall and a temperature-control outer wall, may have a spacing of a few millimeters to one another, and may be spaced apart from one another for example by between 5 mm and 40 mm.

The inner side of the temperature-control cavity wall, that is to say the temperature-control inner wall facing toward the vessel interior space, may in this case be formed so as to directly join the vessel interior space and/or the illumination device. In other words, it is possible for no further element of the device to be formed between the vessel interior space and the temperature-control cavity wall. In other words, the temperature-control cavity wall may thus at least partially directly surround and/or delimit the vessel interior space and/or the illumination device.

Here, "at least partially surround" means that the temperature-control cavity wall surrounds the vessel interior space at its outer surface over at least 40%, preferably over at least 60%, particularly preferably over at least 70%, particularly preferably over at least 80% thereof. In particular, this may mean that the vessel interior space is fully surrounded and/or bordered and/or temperature-controlled by the temperature-control cavity wall aside from an upper cover region and possible viewing window and/or a door opening.

The temperature-control cavity wall may be formed as a pressure appliance in accordance with the PED guideline ("Pressure Equipment Directive" for the European Economic Area) and/or in accordance with the ASME guideline ("American Society of Mechanical Engineers" for the American Economic Zone), in particular as a pressure appliance with approximately 6 barg.

In general, the temperature-control medium may be formed as a fluid such as for example a liquid or a gas, which is situated in a closed temperature-control circuit. The temperature-control cavity wall of the receiving vessel constitutes at least a part of said temperature-control circuit.

In one embodiment, the receiving vessel is designed to receive disposable vessels with a volume of at least approximately 50 liters, preferably at least 1000 liters, particularly preferably at least approximately 2000 liters. In the case of known devices, it has hitherto not been possible for disposable vessels of such large volumes to be efficiently illuminated and cultivated. The impingement of light required for this purpose is made possible for the first time by the particularly efficient illumination and cooling by means of the device according to the invention. It must be noted here that, although the light emitted by the illumination device under some circumstances does not penetrate fully into the middle of the medium in the disposable vessel, it is nevertheless possible for adequately uniform illumination of the medium to be provided by virtue of the medium being mixed by means of an agitation device.

In one embodiment, the device satisfies the GMP guidelines. The GMP guidelines, which is an abbreviation for "Good Manufacturing Practice", are guidelines concerning requirements with regard to hygiene, premises, equipment, documentation and inspections in the pharmaceutical sector. The device may be designed so as to satisfy the requirements stated in the GMP guidelines, in particular the requirements with regard to sterility.

A second aspect relates to a method for receiving a disposable vessel, having the steps:

receiving a disposable vessel in a vessel interior space of a receiving vessel with at least one receiving vessel wall which delimits the vessel interior space;

illuminating the disposable vessel arranged in the vessel interior space by means of an illumination device which is arranged on an inner side, facing toward the vessel interior space, of the receiving vessel wall; and controlling the temperature of the receiving vessel wall.

The method can be performed in particular by means of the device according to the first aspect. Therefore, all of the statements made in the context of the device also apply to the method according to the second aspect, and vice versa.

The invention will be described in more detail below on the basis of exemplary embodiments shown in figures. Identical reference signs are used to denote identical or similar components of the embodiments. Individual features of the embodiments may be combined with other embodiments.

DETAILED DESCRIPTION

Figure 1:
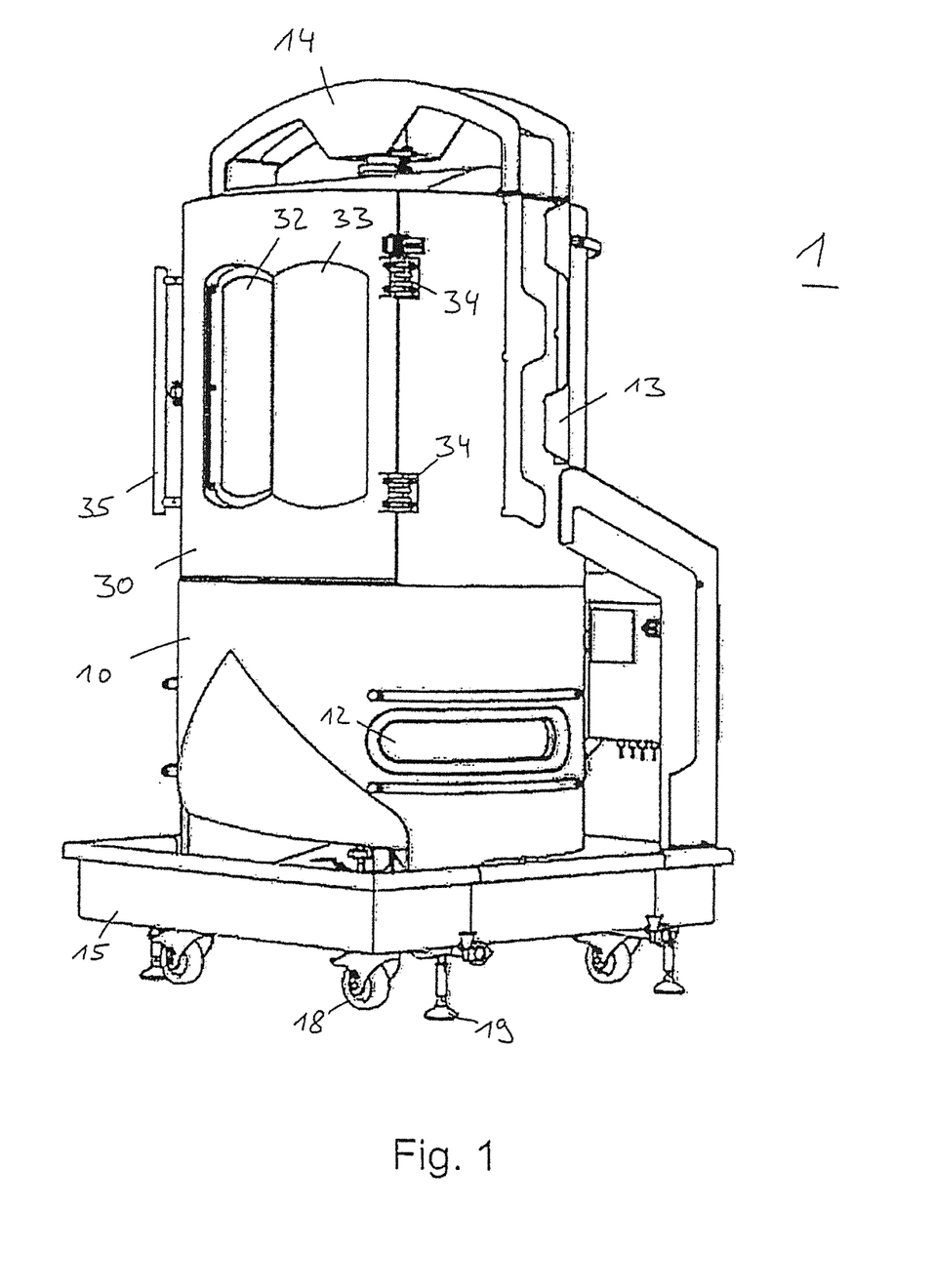
FIG. 1 shows, in a perspective illustration, a device for receiving a disposable pouch.

FIG. 1 shows, in a perspective illustration, a device 1 for receiving a disposable pouch as a disposable vessel. The device 1 shown in the figures may be formed as a constituent part of a system for receiving a disposable pouch.

The device 1 has a receiving vessel 10 which has substantially the shape of a vertically arranged cylinder, that is to say whose cylinder axis is arranged substantially vertically. The receiving vessel 10 has a vessel interior space into which a disposable pouch can be inserted, which disposable pouch may for example contain a biological medium. The biological medium in the disposable pouch is stored and/or illuminated in the vessel interior space of the receiving vessel 10 over a predeterminable time period. While the disposable pouch with the biological medium is situated in the interior of the receiving vessel 10, various reactions may occur with or in the biological medium. The device 1 may thus also be formed as a bioreactor.

For the observation of the biological medium, one or more viewing windows is or are formed in the side walls, through which viewing window(s) it is possible to look from the outside through the receiving vessel wall into the vessel interior space of the receiving vessel 10 in order to observe the biological medium. For this purpose, the device 1 has two base viewing windows 12 in the lower third, and has a door viewing window 32. The base viewing windows 12 are substantially in the form of an elongate oval, the long oval axis of which is oriented substantially horizontally along the curved cylinder outer wall of the receiving vessel 10. The door viewing window 32 is substantially in the form of an elongate rectangle, wherein the longer sides thereof are oriented substantially vertically and are formed in the middle of a single-leaf door 30 in the vessel wall of the receiving vessel 10.

Figure 2A:
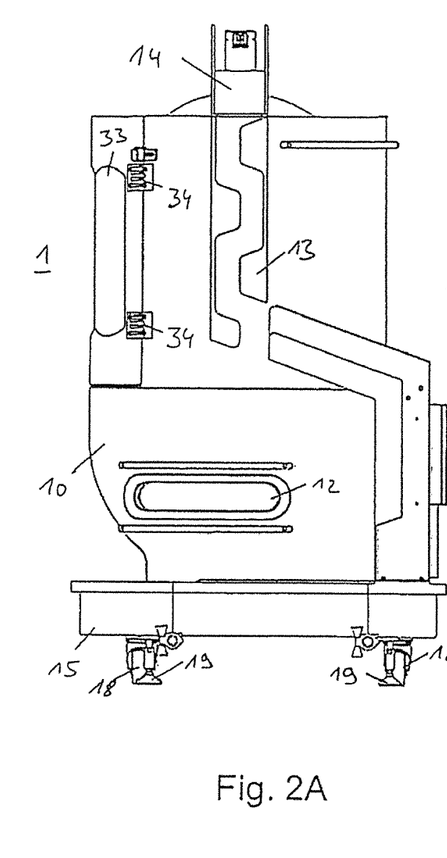
FIG. 2A shows, in a first side view, a device for receiving a disposable pouch.
Figure 2B:
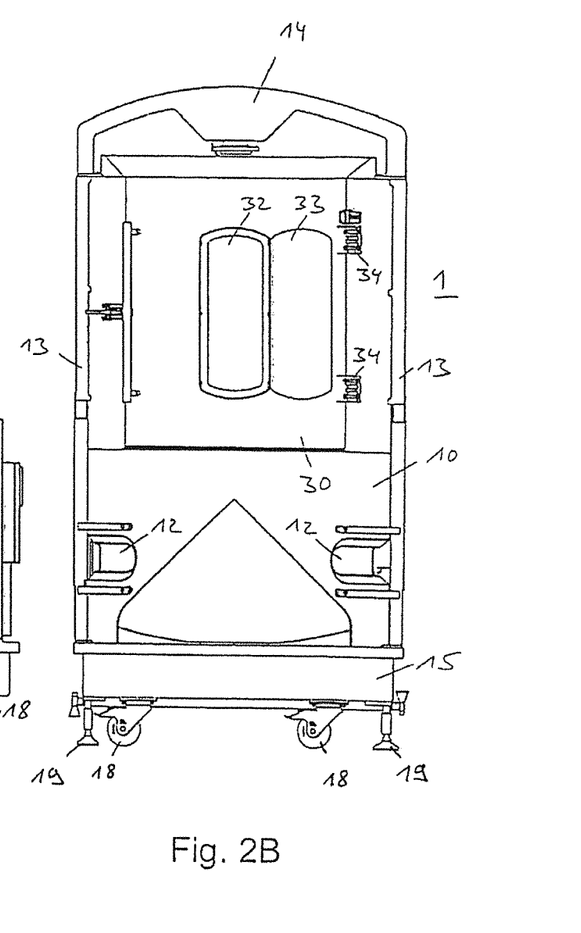
FIG. 2B shows, in a second side view, a device for receiving a disposable pouch.

FIGS. 2A and 2B, together with FIG. 1, show different views of the device 1. Accordingly, for example, FIG. 2B shows a frontal side view toward the single-leaf door 30. The single-leaf door 30 extends in width, that is to say in a horizontal direction, approximately over a cylinder segment of the receiving vessel 10 of approximately 100°. In a horizontal direction, the single-leaf door 30 extends from two door hinges 34 along the cylinder casing to a door handle 35 at the opposite door end. The single-leaf door 30 is formed substantially in the upper two thirds of the receiving vessel 10, whereas the lower third of the receiving vessel 10 is substantially in the form of a rigid base shell, which itself is not of openable design. The single-leaf door 30 is rotatable about the door hinges 34 and is thus openable. When the single-leaf door 30 is open, a door opening is formed at a lateral position in the receiving vessel 10, through which door opening access is provided to the vessel interior space of the receiving vessel 10. It is for example possible for the disposable pouch to be inserted through the door opening from a lateral direction, that is to say substantially in a horizontal movement direction, into the vessel interior space of the receiving vessel 10.

The device 1 is mounted in rollable fashion on rollers 18, on which the device can be pushed in rolling fashion through a room. In addition to the rollers 18, the device 1 may, at the lower end, have fixing feet 19 which serve for the fixing and correct alignment of the device 1, for example on uneven floors.

The receiving vessel 10 is of upwardly open form. In place of a cylinder cover, the receiving vessel 10 has an agitation opening. Above the upwardly open receiving vessel 10, there is formed an agitation device 14 through which an agitation rod can be connected through the agitation opening to the disposable pouch such that the interior of the disposable pouch can be thoroughly mixed. The agitation rod may be arranged in the interior of the disposable pouch and may be connected to the agitation device 14 by means of a coupling or clutch. The agitation device 14 is formed centrally above the receiving vessel 10 and is supported by a carrier bridge which lies on an upper edge of the receiving vessel 10 at mutually opposite side walls of the receiving vessel 10.

FIG. 2A shows a side view toward one of the two laterally arranged cable guides 13. The second of the two cable guides 13 is arranged on the opposite outer wall of the receiving vessel 10. The side view of FIG. 2A shows the device 1 in a position rotated through 90° in relation to the side view of FIG. 2B.

Figure 3:
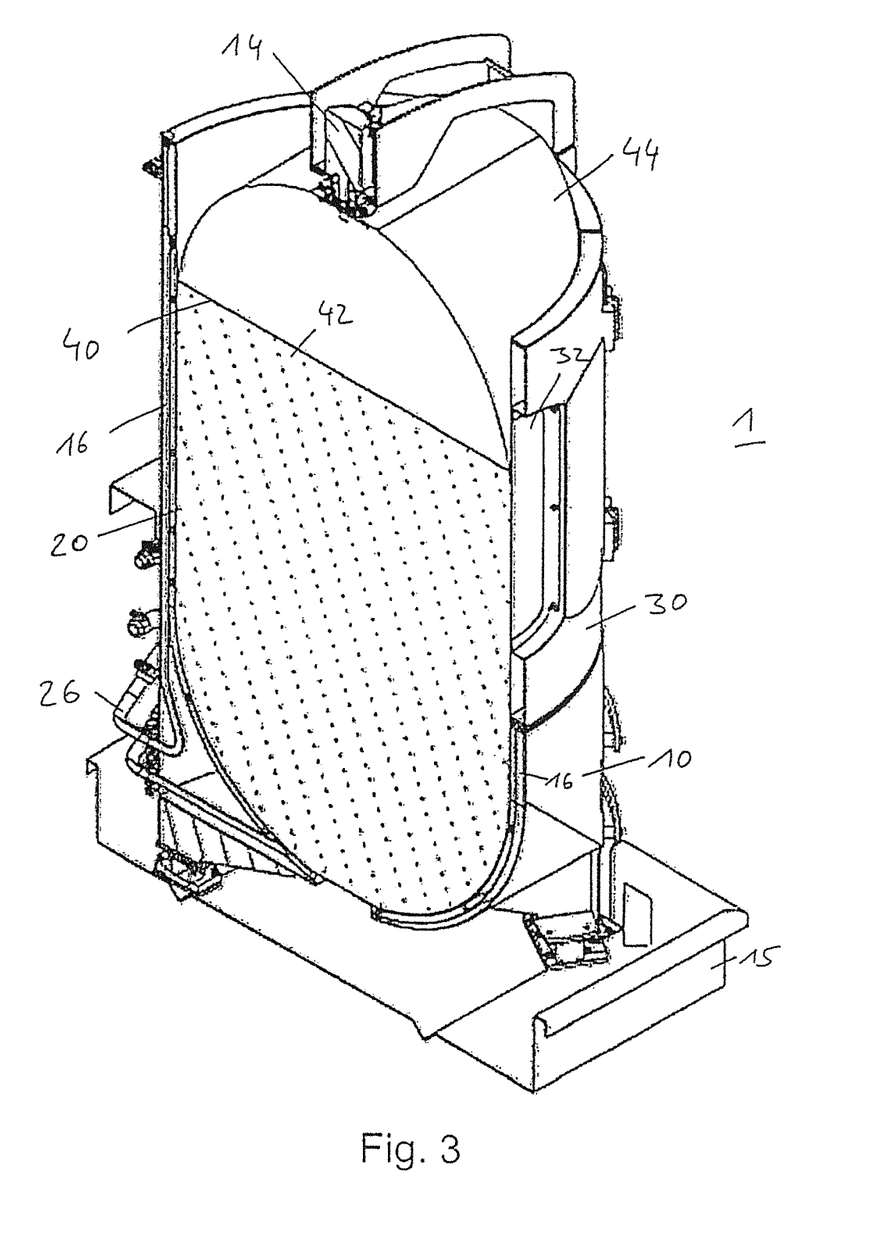
FIG. 3 shows, in a perspective illustration, a vertical sectional view through a device for receiving a disposable pouch.

FIG. 3 shows, in a perspective illustration, a view of a vertical section through the device 1; an illustration of an illumination device has been omitted. FIG. 3 shows for example a disposable pouch 44 as a disposable vessel, more specifically a section through said disposable pouch 44, which is arranged in the vessel interior space of the receiving vessel 10. In the vessel interior space of the receiving vessel 10, and at the same time also in the interior of the disposable pouch 44, there is arranged a biological medium 42, which is filled up to the height of a predetermined fill level height 40. The biological medium 42 extends from the base of the receiving vessel 10 to the fill level height 40 and thus fills the entire internal volume of the receiving vessel 10 up to the fill level height 40, minus the volume of the walls of the disposable pouch 44 and of an illumination device (not shown).

The disposable pouch 44 is held in shape by a vessel wall 16 of the receiving vessel 10, which vessel wall may extend upward from the rounded base of the receiving vessel 10 beyond the fill level height 40. At least along the upper half, preferably along the upper two thirds of the receiving vessel 10, a receiving vessel wall 16 may extend substantially vertically upward in a vertical direction.

The receiving vessel walls 16 of the receiving vessel are formed at least partially as a temperature-control cavity wall 20 in which a temperature-control medium (not shown in the figures) flows. The temperature-control medium may be regulated to a low pressure of below 0.5 bar, or to a pressure of up to approximately 6 barg. The temperature-control cavity wall 20 may extend over the entire base or the entire base shell of the receiving vessel 10 and upward from the vessel base along the receiving vessel walls 16, beyond the fill level height 40 up to a predeterminable temperature-control height. The temperature-control height may be arranged substantially 1 cm to 20 cm vertically above the fill level height 40.

The biological medium 42 may be in thermal contact with the temperature-control cavity wall 20, from which said biological medium is separated only by means of the thin pouch wall of the disposable pouch 44 and, at least partially, an illumination device (not shown). The biological medium 42 and/or the illumination device can be regulated to a predeterminable temperature by means of the temperature-control medium.

The device 1 may in particular be designed and provided for controlling the temperature of the vessel interior space and of the illumination device arranged therein to a predeterminable setpoint temperature of approximately 0° C. to approximately 80° C., preferably of approximately 20° C. to approximately 40° C.

The temperature-control cavity wall 20 surrounds the vessel interior space of the receiving vessel 10 almost completely up to a point above the fill level height 40. In the exemplary embodiments shown in the figures, to "surround almost completely" means that the temperature-control cavity wall 20 surrounds the vessel interior space completely up to the temperature-control height aside from the positions at which the possibly provided base viewing windows 12 are arranged and at which the at least one single-leaf door 30 is arranged. At the positions of the base viewing windows 12, there may be arranged a glass pane which provides a view of the vessel interior space and in particular of the biological medium 42 situated in the receiving vessel 10 (and possibly a corresponding blackout means without temperature control). At the position of the single-leaf door 30, an aperture in the form of the door opening 36 is situated in the temperature-control cavity wall 20. In an alternative embodiment, a temperature-control cavity wall may also be formed on the inner side of the single-leaf door 30, which temperature-control cavity wall is supplied with the temperature-control medium via temperature-control lines arranged on the door hinges 34.

In general, to "surround almost completely" may mean that the temperature-control cavity wall 20 surrounds the vessel interior space completely up to the temperature-control height aside from a certain few predetermined positions. Said certain few positions may be the positions at which viewing windows are arranged in the vessel wall of the receiving vessel 10, and possibly at which the single-leaf door 30 is arranged. In general, the temperature-control cavity wall 20 does not delimit the vessel interior space at its upper end.

The temperature-control cavity wall 20 may, at its outer side, that is to say at the side averted from the vessel interior space, be surrounded by an insulating cavity wall in which an insulator is situated. The insulating cavity wall may surround the receiving vessel 10 almost completely from the base of the receiving vessel 10 up to the upper end of the receiving vessel wall 16 (in this regard, cf. also FIG. 3). The insulating cavity wall insulates both the vessel interior space and in particular the temperature-control cavity wall 20 to the outside. By means of the insulator arranged in the insulating cavity wall, directed temperature control by means of the temperature-control medium in the inward direction toward the vessel interior space and/or toward the illumination device is provided, which increases the energy efficiency of the device 1.

Temperature-control lines may be connected to the interior of the temperature-control cavity wall 20. The device may furthermore have ports and/or insulating lines for providing a vacuum in the insulating cavity wall, though these are not shown in the figures.

The temperature-control height may exceed the predetermined fill level height 40 and also the contact area of the disposable pouch 44 with the receiving vessel walls 16 of the receiving vessel 10.

The disposable pouch 44 is, after use, emptied for example via an outlet arranged below the device 1, and can subsequently be disposed of entirely. Through the use of the disposable pouch 44 in a single-use process, cleaning of the device 1 can be eliminated, or can be performed much more quickly.

A collecting trough 15 may serve as a collecting element if biological medium escapes from the device 1 for example owing to a leak in the disposable pouch.

Air, a vacuum, an insulation wool, a glass wool, a rock wool or a similar insulating material may be used as an insulator in the insulating cavity wall.

In the interior of the temperature-control cavity wall 20, the device 1 has the fewest possible thermal bridges, that is to say for example continuous metallic connections from the vessel interior space to the exterior space, which would slow the temperature control of the vessel interior space. The device 1 may have only thermal bridges that are statically required and/or statically imperatively necessary.

The temperature-control medium is situated in the interior of a closed temperature-control system which comprises the interior of the temperature-control cavity wall 20. The regulation and/or control of the temperature of the temperature-control medium may be performed by means of an internal, electrically operated heating device, and optionally or alternatively by means of an external heat exchanger. Both cooling and heating of the temperature-control medium can be performed by means of the external heat exchanger independently of the internal electric heating device of the temperature-control system.

Figure 4:
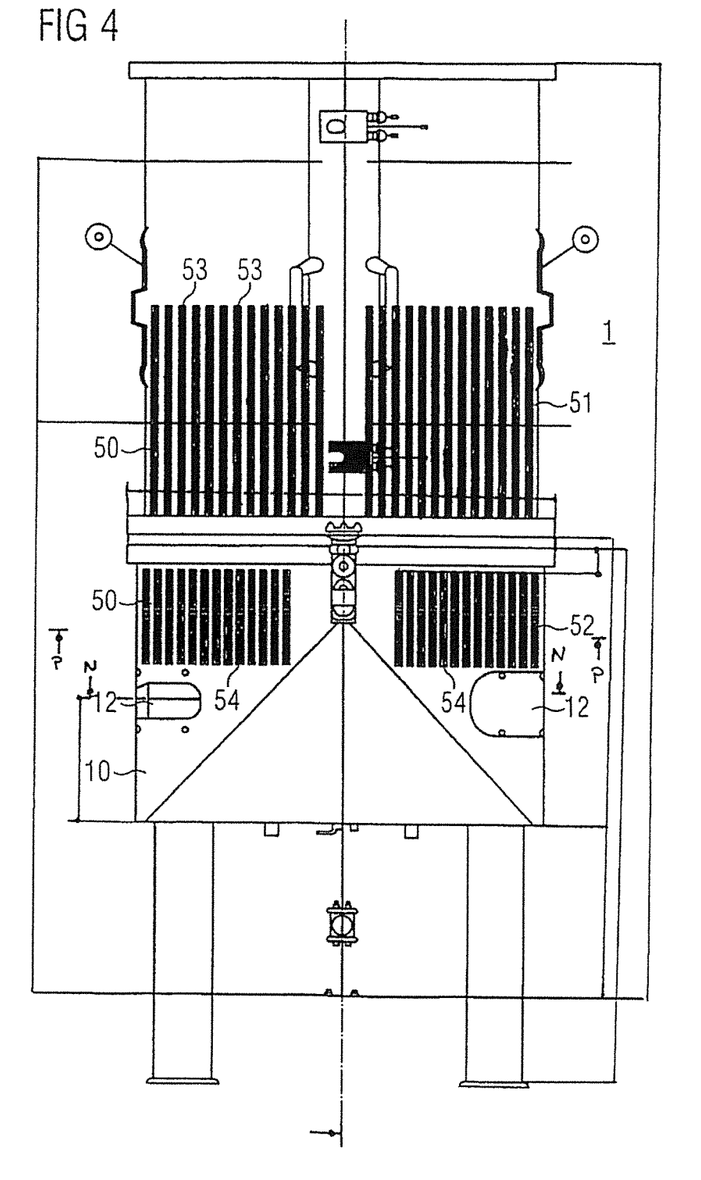
FIG. 4 shows, in a schematic illustration, a device for receiving a disposable pouch having an illumination device.

FIG. 4 shows, in a schematic illustration, a device having the receiving vessel 10, in which a multi-part illumination device 50 is arranged. The illumination device 50 has a first, upper illumination unit 51 and a second, lower illumination unit 52. In general, the illumination device 50 may have multiple illumination units 51, 52 which may for example be arranged one above the other, as in the exemplary embodiment shown.

Here, FIG. 4 shows a schematic illustration of the device in which, in particular, the temperature-control unit and the double-walled receiving vessel wall that have been described with reference to the preceding figures are not shown. The device 1 may however have all of the elements of the device described with reference to the preceding figures.

The illumination device 50 is arranged in the interior of the receiving vessel 10. Here, the upper illumination unit 51 is arranged in an upper part of the receiving vessel 10, whereas the lower illumination unit 52 is arranged in a lower part of the receiving vessel 10, for example in the interior of a base shell of the receiving vessel 10. The upper illumination unit 51 is arranged in the upper part of the receiving vessel 10, on which the single-leaf door 30 for the insertion of the disposable vessel is also arranged (cf. for example FIG. 1). The upper illumination unit 51 may be of substantially ring-shaped form, wherein the ring is arranged in the interior of the receiving vessel 10 along the circumference, and thus along the inner side of the receiving vessel wall 16. Here, the ring central point of the upper illumination unit 51 substantially coincides with the cylinder axis of the receiving vessel 10.

Similarly, the lower illumination unit 52 is also of substantially ring-shaped form, specifically along the inner side of the lower part of the receiving vessel 10. The central point of the ring of the lower illumination unit 52 also lies substantially on the cylinder axis of the receiving vessel 10.

The upper illumination unit 51 has a multiplicity of upper illumination carriers 53 which are of substantially rod-shaped and/or strip-shaped form. The upper illumination carriers 53 are oriented substantially parallel to one another and are formed as vertically arranged strips. The upper illumination carriers 53 may each support one or more light sources, which radiate light into the vessel interior of the receiving vessel 10.

Similarly, the lower illumination unit 52 also has a multiplicity of lower illumination carriers 54. The lower illumination carriers 54 are of substantially rod-shaped and/or strip-shaped form, and are arranged in a substantially vertical direction along the inner side of the receiving vessel 10. Both the upper illumination carriers 53 and the lower illumination carriers 54 serve for supporting light sources of the illumination device 50. The strip width of the illumination carriers 53 and 54 in a horizontal direction is in this case much smaller than the strip length in a vertical direction. By means of this arrangement, the strip-shaped illumination carriers 53 and 54 can be adapted particularly expediently and easily to the rounded cylinder inner wall of the receiving vessel 10.

In the exemplary embodiment shown, the lower illumination carriers 54 have a smaller vertical extent than the upper illumination carriers 53. The vertical extent of the respective illumination carriers 53 and 54 may be dependent on the vertical height available in the interior of the respective part of the receiving vessel 10. For example, the upper part of the receiving vessel 10, in which the upper illumination unit 51 is arranged, is taller than the lower part of the receiving vessel 10, in which the lower illumination unit 52 is arranged. In other exemplary embodiments, this may be reversed, or else the upper and lower illumination carriers 53 and 54 may be of substantially equal length.

Figure 5A:
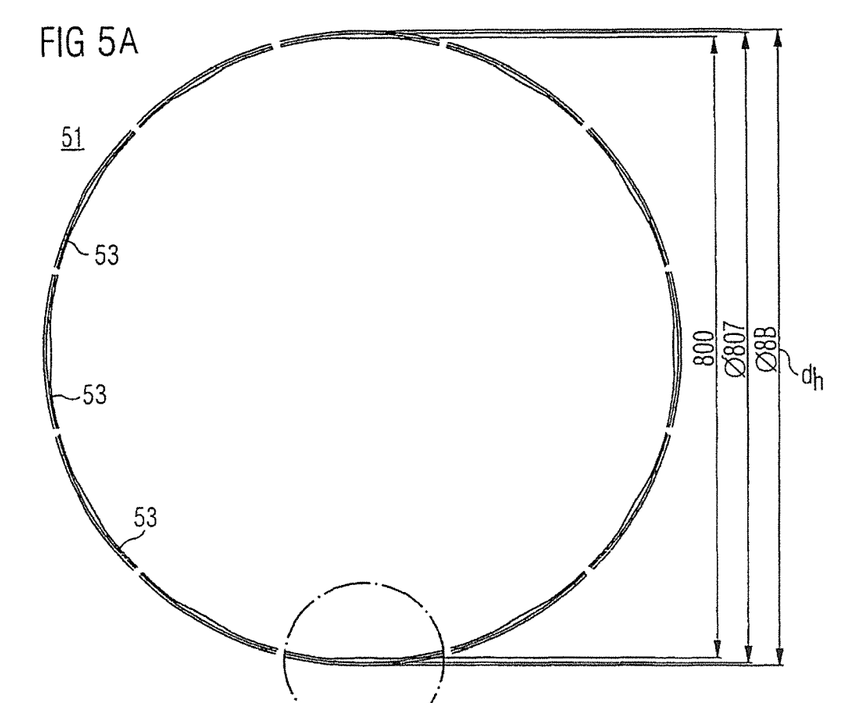
FIG. 5A shows a schematically illustrated cross section through an illumination device for a receiving vessel.

FIG. 5A shows a highly schematic horizontal cross section through the first, upper illumination unit 51. The upper illumination unit 51 is designed and provided for being inserted into the vessel interior space of the receiving vessel 10. The receiving vessel 10 has, in the horizontal cross section, a substantially circular receiving vessel wall 16. Said receiving vessel wall 16 may, as stated above, be formed as a temperature-control cavity wall 20.

As shown in FIG. 5A, the cross-sectional shape of the upper illumination unit 51 is adapted to the cross section through the upper part of the receiving vessel 10. Thus, both the receiving vessel 10 and the upper illumination unit 51 have, in the horizontal cross section, a substantially circular shape, wherein the two circle diameters are of approximately equal size.

The upper illumination unit 51 has a multiplicity of curved, upper illumination carriers 53. Each of the upper illumination carriers 53 has an outwardly convex curvature which approximately corresponds to the inwardly concave curvature of the inner side of the receiving vessel wall 16. The upper illumination carriers 53 are arranged along the inner side of the receiving vessel wall 16 over an angle segment of in each case approximately 30°. Thus, the inner side of the receiving vessel wall 16 can be almost completely covered along the cylinder casing by the twelve illumination carriers 53 shown in FIG. 5A. Together, the upper illumination carriers 53 form the upper illumination unit 51 of ring-shaped cross section.

Figure 5B:
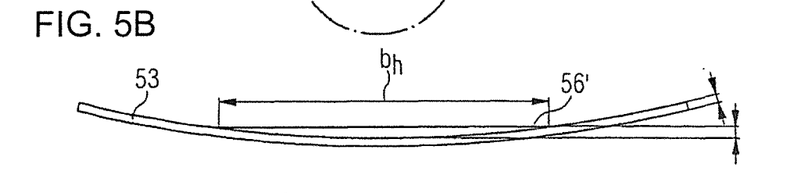
FIG. 5B is a detail of the region of FIG. 5A identified by the dash-dotted circle.

A detail of the cross section is illustrated on an enlarged scale in FIG. 5B, said detail being marked by a dash-dotted circle in FIG. 5A.

In this enlarged cross section, it is shown that the individual upper illumination carriers 53 are of curved form in the horizontal cross section. The illumination carriers 53 may have circuit boards 56 (in this regard, cf. also FIGS. 6A and 6B) for the actuation of the light sources, which circuit boards are normally initially produced without a curvature. The circuit boards 56 may likewise be arranged in curved fashion on the upper illumination carriers 53. To prevent damage to the circuit boards 56, the curvature of the circuit boards 56 out of the planar shape is as slight as possible here. Therefore, the upper and lower illumination carriers 53, 54 are formed such that, in the horizontal cross section, they cover an angle segment of at most approximately 45° of the inner side of the receiving vessel wall 16, preferably at most approximately 30°, particularly preferably at most approximately 20°.

Alternatively or in addition, it is also possible for non-curved circuit boards 56' to be arranged on the upper and lower illumination carriers 53, 54, for example laid into the curved illumination carriers 53, 54, as is schematically denoted in FIG. 5 by the reference designation of the non-curved circuit boards 56'. To permit the best possible adaptation of the non-curved circuit boards 56' to the illumination carriers 53 and thus to the receiving vessel wall 16, the horizontal extent, shown in FIG. 5, of the upper, non-curved circuit boards 56' is formed so as to be significantly smaller than the diameter of the horizontal cross section through the receiving vessel 10. Thus, a longest horizontal extent bh of the circuit boards 56' may amount to between 1% and 15% of the horizontal internal diameter dh of the receiving vessel 10, preferably between 1% and 10%, particularly preferably between 1% and 5%.

This yields the vertical strip-shaped form of the illumination carriers 53 and 54 shown in FIG. 4.

A similar or identical situation may apply to the lower illumination carrier 54, which is not shown in FIG. 5.

Figure 6A:
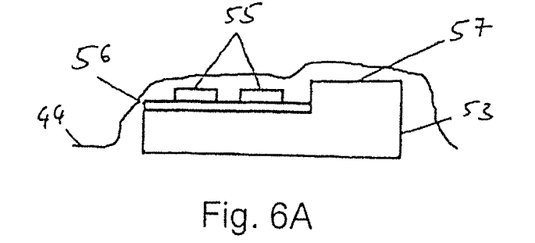
FIG. 6A shows a schematically illustrated cross section through a detail of an illumination carrier.

FIG. 6A shows a schematic cross section through a detail of an illumination unit, for example the upper illumination unit 51 or the lower illumination unit 52, in particular a horizontal cross section through one of the illumination carriers. Here, a main body of the upper illumination carrier 53, for example, may be of metallic form, in particular as a holder composed of a metal such as for example aluminum with a high thermal conductance coefficient. The main body may, at an outer side 53a, be in direct mechanical contact, and thus heat-exchanging contact, with the inner side of the receiving vessel wall 16. A circuit board 56 is arranged on an inner side or inner wall of the upper illumination unit 51, for example. Multiple light sources 55, for example LEDs, are arranged on the circuit board 56. The light sources 55 are oriented so as to radiate light in the direction of the vessel interior space, for example substantially toward the cylinder axis of the receiving vessel 10, which runs through the central point of the circular cross section shown in FIG. 5.

A pouch wall of the disposable vessel 44 may bear substantially directly against the light sources 55. Since the wall of the disposable vessel 44 may be of flexible form, in particular composed of a flexible material, the shape of the disposable vessel 44 can substantially adapt to the inner profile of the upper illumination unit 51. On and/or adjacent to the upper illumination carriers 53, the upper illumination unit 51 may furthermore have one or more webs 57, which form a thermal bridge between the disposable pouch 44 and the receiving vessel wall 16.

Figure 6B:
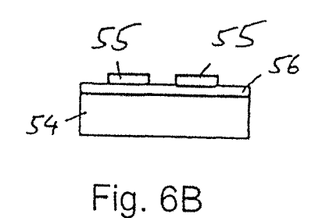
FIG. 6B shows a schematically illustrated cross section through a detail of an illumination carrier.

FIG. 6B shows a schematic cross section through a detail of an illumination unit with a main body, for example a horizontal cross section through one of the lower illumination carriers 54 of the lower illumination unit 52. The lower illumination carrier 54, for example, may be of metallic form (composed for example of aluminum). The main body of the lower illumination carrier 54 may, at an outer side 54a, be in direct mechanical contact, and thus heat-exchanging contact, with the inner side of the receiving vessel wall 16. On an inner side situated opposite the outer side 54a, there is arranged a circuit board 56, on which light sources 55 (for example LEDs) are arranged.

In general, both the upper illumination unit 51 and the lower illumination unit 52 may have one or more of the illumination carriers 53 and/or 54, and one or more of the webs 57. In FIG. 6B, an illustration of the wall of the disposable pouch 44 has been omitted. Here, FIGS. 6A and 6B are given as schematically illustrated examples, which need not imperatively relate to details of the upper illumination unit 51 or of the lower illumination unit 52.

Both illumination units 51, 52 may be arranged in substantially ring-shaped fashion along the inner circumference of the receiving vessel 10.

The circuit boards 56 with the light sources 55 may be arranged in exchangeable fashion on the upper and/or lower illumination unit 51 and/or 52 in order to be able to vary a radiation spectrum of the light sources 55.

By means of the device 1 with the illumination device 50, a technology platform is provided with which, through corresponding population with circuit boards 56, 56' and light sources 55, different usage situations can be covered and with which a biological medium in the bioreactor can be irradiated with light, in particular also with UV light, IR light, laser light, modulated light etc. A controller or electrical line for the supply of electricity to the light sources 55 may be laid into the interior of the receiving vessel 10 via the agitation opening and/or the cable guide 13. The upper and/or lower illumination unit 51 and/or 52 may, as a substantially flat profile, in particular aluminum profile, be adhesively bonded and/or screwed to the inner side of the outer vessel wall 16.

The temperature-control unit 20 may in particular be provided for controlling the temperature of the receiving vessel wall 16 to a temperature between 10 and 60° C., in particular of 27° C. to 37° C. The upper part of the receiving vessel 10 shown in FIG. 4, in which the upper illumination unit 51 is arranged, may have two doors instead of the single-leaf door 30, by means of which doors the receiving vessel 10 can be fully opened at least in the upper part. A half-ring-shaped element of the upper illumination unit 51 is arranged in the interior of each of the two doors.

Control and/or electrical cables for the illumination device 50 may be laid to the light sources 55 either via the agitation opening or through one of the windows.

The device may have a safety function in the case of which the illumination device 50 is automatically deactivated if the door(s) of the receiving vessel 10 is/are opened.

In alternative embodiments of the illumination device that are not shown in the figures, the illumination device may have at least one flexible LED band which may be arranged along the inner side of the receiving vessel, for example along the inner circumference. The LED bands may be arranged substantially horizontally along the inner circumference, and may for example each end at the door opening. LED bands may also be arranged horizontally and/or vertically on the inner side of the single-leaf door, for example from one end of the door leaf to an opposite end of the door leaf.

LIST OF REFERENCE DESIGNATIONS

1 Device
10 Receiving vessel
12 Base viewing window
13 Cable guide
14 Agitation device
15 Collecting trough
16 Receiving vessel wall
18 Rollers
19 Fixing feet
20 Temperature-control cavity wall
30 Single-leaf door
32 Door viewing window
33 Door blackout means
34 Door hinge
35 Door handle
36 Door opening
40 Fill level height
42 Biological medium
44 Disposable vessel or disposable pouch
50 Illumination device
51 Upper illumination unit
52 Lower illumination unit
53 Upper illumination carrier
53a Outer side of the upper illumination carrier
54 Lower illumination carrier
54a Outer side of the lower illumination carrier
55 Light source
56 Circuit board
56' Circuit board
57 Web
$b_h$ Horizontal extent of an illumination carrier
$d_h$ Horizontal internal diameter of the receiving vessel

The invention claimed is:

1. A device (1) for receiving biological media, comprising:
 a receiving vessel (10) with at least one receiving vessel wall (16) that delimits a vessel interior space of the receiving vessel (10), the receiving vessel wall (16) having an inner side facing toward the vessel interior space of the receiving vessel (10);
 a disposable vessel (44) having flexible walls and being arranged within the vessel interior space of the receiving vessel (10);
 an illumination device (50) arranged on the inner side of the receiving vessel wall (16) so that the illumination device (50) is between the receiving vessel wall (16) and the flexible walls of the disposable vessel (10), the illumination device (50) being designed to radiate light into the vessel interior space of the receiving vessel (10), the illumination device (50) being comprised of a plurality of illumination carrier strips (53, 54) aligned substantially parallel to one another and extending substantially vertically on the inner side of the receiving vessel wall, each of the illumination carrier strips (53, 54) having opposite first and second sides, multiple light sources arranged on the first side of each of the illumination carrier strips (53, 54) and facing the disposable vessel (44) interior space, the second side of each of the illumination carrier strips (53, 54) facing the at least one receiving vessel wall (16);
 a temperature-control cavity (20) formed as part of the receiving vessel wall (16) and accommodating a cooling medium therein; and
 a temperature-control unit for controlling a flow of the cooling medium in the temperature-control cavity (20) of the receiving vessel wall (16) for dissipating heat produced by the illumination device (50) and controlling a temperature in the disposable vessel (40).

2. The device of claim 1, wherein the illumination device (50) is arranged at a position of the inner side of the receiving vessel wall (16) that is temperature-controlled by the temperature-control unit directly at an outer side, averted from the vessel interior space, of the receiving vessel wall (16).

3. The device of claim 1, wherein the at least one receiving vessel wall (16) comprises plural lateral receiving vessels walls (16) and inner sides disposed respectively on the lateral receiving walls (16), and wherein the illumination device (50) is arranged to be distributed over at least 50% of an area of the inner sides of all lateral receiving vessel walls (16).

4. The device of claim 1, wherein the illumination device (50) has a multiplicity of actuatable LEDs as light sources (55).

5. The device of claim 1, wherein the illumination device (50) radiates at least 90% of the radiated luminous power with a predetermined wavelength and/or in a predetermined wavelength spectrum between 50 nm and 50 μm.

6. The device of claim 1, wherein the illumination device (50) is designed to radiate light by means of exchangeable light sources (55) that have different radiation spectra.

7. The device of claim 1, wherein an external shape of an outer side (53a, 54a), averted from the vessel interior space, of the illumination device (50) is adapted to an internal shape of the inner side of the receiving vessel wall (16).

8. The device of claim 7, wherein the external shape of the illumination device (50) is of convex form and the internal shape of the receiving vessel wall (16) is of concave form.

9. The device of claim 1, wherein the illumination device (50) is designed to radiate light with a luminous power of up to approximately 3000 μmol/m²s into the vessel interior space.

10. The device of claim 1, wherein, in an operational position of the device (1), the disposable vessel (44) is in physical contact with the illumination device (50).

11. The device of claim 1, wherein the illumination device includes a transparent resin layer and/or lacquer layer with a thickness of up to approximately 1 mm is arranged over the light sources (55) of the illumination device (50).

12. The device of claim 1, wherein the illumination device (50) has at least one thermal bridge between the light sources (55) of the illumination device (50) and the temperature-controlled receiving vessel wall (16).

13. The device of claim 1, wherein the temperature-control unit is designed to impart a heat removal power of up to at least 8 kW.

14. The device of claim 1, wherein the receiving vessel (10) is designed to receive disposable vessels (44) with a volume of at least approximately 500 liters.

15. A method for receiving a disposable vessel (44), comprising the steps:
   providing a receiving vessel (10) having at least one receiving vessel wall (16) that delimits a vessel interior space;
   positioning a plurality of illumination carrier strips (53, 54) in the vessel interior space of the receiving vessel (10) so that the illumination carrier strips (53, 54) are aligned substantially parallel to one another and extend substantially vertically, each of the illumination carrier strips (53, 54) having opposite first and second sides, multiple light sources being arranged on the first side of each of the illumination carrier strips (53, 54), the positioning of the illumination carrier strips (53, 54) being carried out so that the light sources face the interior space of the receiving vessel (10) and so that the second side of each of the illumination carrier strips faces the at least one receiving vessel wall (16);
   providing a disposable vessel (44) having flexible walls;
   receiving the disposable vessel (44) in the vessel interior space of the receiving vessel (10) so that the illumination carrier strips (53, 54) are between the at least one receiving vessel wall (16) and the flexible walls of the disposable vessel (44);
   illuminating the disposable vessel (44) by the illumination device (50) that is arranged on an inner side, facing toward the vessel interior space, of the receiving vessel wall (16) and between the receiving vessel wall (16) and the disposable vessel (10); and
   directing a cooling fluid through the receiving vessel wall (16) for removing illumination induced heat.

\* \* \* \* \*